United States Patent
Shanks et al.

(10) Patent No.: US 12,329,961 B2
(45) Date of Patent: Jun. 17, 2025

(54) IMPLANT INCLUDING NANOGENERATOR

(71) Applicant: IntelliFuse LLC, Union City, TN (US)

(72) Inventors: Todd Shanks, Dallas, TX (US); George Alexander Jones, River Forest, IL (US)

(73) Assignee: INTELLIFUSE LLC, Union City, TN (US)

(*) Notice: Subject to any disclaimer, the term of this patent is extended or adjusted under 35 U.S.C. 154(b) by 366 days.

(21) Appl. No.: 17/875,310

(22) Filed: Jul. 27, 2022

(65) Prior Publication Data

US 2024/0033503 A1  Feb. 1, 2024

(51) Int. Cl.
*A61N 1/05* (2006.01)
*A61N 1/32* (2006.01)

(52) U.S. Cl.
CPC ............... *A61N 1/05* (2013.01); *A61N 1/326* (2013.01)

(58) Field of Classification Search
CPC ......... A61N 1/05; A61N 1/326; A61N 1/3785
USPC ....................................................... 310/319
See application file for complete search history.

(56) References Cited

U.S. PATENT DOCUMENTS

| | | | |
|---|---|---|---|
| 6,247,371 B1 * | 6/2001 | Namerikawa | G01P 15/0802 73/862 |
| 7,618,647 B2 | 11/2009 | Weber et al. | |
| 7,729,768 B2 * | 6/2010 | White | A61N 1/3785 310/354 |
| 9,005,648 B2 | 4/2015 | Jin et al. | |
| 9,035,534 B2 | 5/2015 | Miao | |
| 9,597,434 B2 | 3/2017 | Kipper et al. | |
| 10,874,774 B2 | 12/2020 | Kucera et al. | |
| 2006/0229715 A1 | 10/2006 | Istephanous et al. | |
| 2010/0255447 A1 | 10/2010 | Biris et al. | |
| 2013/0261764 A1 | 10/2013 | Guerra et al. | |
| 2019/0009083 A1 * | 1/2019 | Webster | A61N 1/025 |
| 2022/0193425 A1 * | 6/2022 | Makdissi | A61N 1/37217 |
| 2023/0149720 A1 * | 5/2023 | Li | A61N 1/37 607/35 |
| 2024/0033508 A1 * | 2/2024 | Shanks | H02N 2/18 |

FOREIGN PATENT DOCUMENTS

WO  20203533  * 10/2021

* cited by examiner

*Primary Examiner* — Mark W. Bockelman
(74) *Attorney, Agent, or Firm* — BUSSINESS PATENT LAW, PLLC

(57) ABSTRACT

An implant provided with an auto-generator generating an electric charge. One or more nanogenerators are incorporated into or onto the implant or used as stand-alone devices. It is believed that electric charge improves the healing of damaged/injured tissues.

19 Claims, 4 Drawing Sheets

IMPLANT INCLUDING NANOGENERATOR

BACKGROUND OF THE INVENTION

A. Field of the Invention

Among other things, the present invention is an implant for implantation into an animal. A nanogenerator can be incorporated into the implant or the nanogenerator can be a stand-alone device. Mammalian tissues are well suited for receiving the implant or stand-alone nanogenerator. The novel and nonobvious structures of the present implant and nanogenerator are particularly useful in surgical/medical procedures associated with tissues, surgically created cavities, joint spaces or wounds.

B. Description of the Previous Art

Any discussion of references cited in this Description of the Previous Art merely summarizes the disclosures of the cited references and Applicant makes no admission that any cited reference or portion thereof is relevant prior art. Applicant reserves the right to challenge the accuracy, relevancy and veracity of the cited references.

References that may indicate a state-of-the-art for the current invention include: 1) US Published Patent Application 20190009083A1-Webster et al. discloses a self-powered bone growth stimulator; 2) U.S. Pat. No. 9,005,648B2-Jin et al. discloses inorganically surface-modified polymers and methods for making and using them; 3) US Published Patent Application 20060229715A1-Istephanous et al. discloses incorporating nanotubes and methods for producing the same; 4) U.S. Pat. No. 7,618,647B2-Weber, et al. discloses using bucky paper as therapeutic aid in medical applications; 5) U.S. Pat. No. 9,597,434B2-Kipper et al. discloses surface treatments for vascular stents and methods thereof; 6) U.S. Pat. No. 10,874,774B2-Kucera et al. discloses an active implantable medical device and method of using an active implantable medical device; 7) US Published Patent Application 20130261764A1-Guerra et al. discloses a multifunctional prosthesis with multilayer covering and methods of production thereof; 8) US Published Patent Application 20100255447A1-Biris, et al. discloses advanced bio-compatible polymer surface coating for implant and tissue engineering scaffolds; and 9) U.S. Pat. No. 9,035,534B2-Miao discloses vortex alignment buckypaper generating electricity.

Among other things, none of the above listed references disclose:

1) An implant for implantation into a surgically created cavity, a joint space or a wound; the implant comprising: a) an outward surface; b) a nanogenerator generating an electrical charge; the nanogenerator, positioned within an enclosed chamber of the implant, comprising: a weight suspended by a plurality of suspenders connected to an inward wall surrounding the enclosed chamber; the suspenders comprising a charge generating composition, wherein movement of the weight causes the charge generating composition to generate the electric charge deliverable to an outward section of the device; and c) the outward section comprising: i) a biocompatible electroconductive substance for transferring the electric charge to the surgically created cavity, the joint space or the wound; and ii) optionally, a store adapted to contain a portion of the electric charge and subsequently supply the stored electric charge to the biocompatible electroconductive substance.

2) Another preferred embodiment of the current invention can be described as a biocompatible nanogenerator adapted for surgical/medical use; the biocompatible nanogenerator comprising a weight suspended by a plurality of suspenders connected to an inward wall of a housing; the suspenders comprising a charge generating composition, wherein movement of the weight causes the charge generating composition to generate and deliver an electric charge to a biocompatible electroconductive substance, positioned on an outward section of housing, for distribution of the electric charge to an environment associated with the surgical/medical use.

3) a biocompatible nanogenerator adapted for surgical/medical use; the nanogenerator comprising: a) a biocompatible electroconductive substance, positioned on an outward section of housing, for distributing a generated electric charge to an environment associated with the surgical/medical use; b) one or more charge generating compositions, connected to an inner wall of housing, adapted to generate and deliver the generated electric charge to the biocompatible electroconductive substance; and c) a movable device contacting the one or more charge generating compositions, wherein movement of the movable device moves the one or more charge generating compositions from a resting state, thereby generating the generated electric charge.

SUMMARY OF THE INVENTION

The present invention is a load supporting implant for implantation into an animal. Preferred embodiments of the invention are provided with one or more nanogenerators incorporated into the load supporting implant. Other preferred embodiments of the current invention can be stand-alone biocompatible nanogenerators. The nanogenerators deliver an electric charge to one or more biocompatible electroconductive substances for delivering the electric charge to the environment proximate the biocompatible electroconductive substance. Meeting a long felt but unfilled need in the medical/surgical arts, the novel and unique structures of the present implant and biocompatible nanogenerator(s) can improve healing by providing an auto-generated electric charge to the environment proximate the biocompatible electroconductive substance.

An aspect of the present invention is to provide an implant with one or more nanogenerators for generating an electrical charge.

Still another aspect of the present invention is to provide an implant or nanogenerator with one or more biocompatible outward sections adapted to transfer electrical charge to a surgically created cavity, a joint space, a tissue, a wound or other environment near the implant or the biocompatible nanogenerator.

It is still another aspect of the present invention to provide a nanogenerator that utilizes motion to generate the electric charge.

Yet still another aspect of the present invention is to provide a nanogenerator that uses suspenders and a weight to generate the electric charge.

Still another aspect of the present invention is to provide a nanogenerator that uses carbon molecules to generate at least some of the electric charge.

It is still another aspect of the present invention to provide a nanogenerator that can be incorporated into or onto the implant.

It is still another aspect of the present invention to provide a stand-alone biocompatible nanogenerator adapted to deliver an electric charge to a medical/surgical environment.

A preferred embodiment of the current invention can be described as an implant for implantation into a surgically created cavity, a joint space or a wound; the implant comprising: a) an outward surface; b) a nanogenerator generating an electrical charge; the nanogenerator, positioned within an enclosed chamber of the implant, comprising: a weight suspended by a plurality of suspenders connected to an inward wall surrounding the enclosed chamber; the suspenders comprising a charge generating composition, wherein movement of the weight causes the charge generating composition to generate the electric charge deliverable to an outward section of the device; and c) the outward section comprising: i) a biocompatible electroconductive substance for transferring the electric charge to the surgically created cavity, the joint space or the wound; and ii) optionally, a store adapted to contain a portion of the electric charge and subsequently supply the stored electric charge to the biocompatible electroconductive substance.

Another preferred embodiment of the current invention can be described as a biocompatible nanogenerator adapted for surgical/medical use; the biocompatible nanogenerator comprising a weight suspended by a plurality of suspenders connected to an inward wall of a housing; the suspenders comprising a charge generating composition, wherein movement of the weight causes the charge generating composition to generate and deliver an electric charge to a biocompatible electroconductive substance, positioned on an outward section of housing, for distribution of the electric charge to an environment associated with the surgical/medical use.

Still another preferred embodiment of the current invention can be described as a biocompatible nanogenerator adapted for surgical/medical use; the nanogenerator comprising: a) a biocompatible electroconductive substance, positioned on an outward section of housing, for distributing a generated electric charge to an environment associated with the surgical/medical use; b) one or more charge generating compositions, connected to an inner wall of housing, adapted to generate and deliver the generated electric charge to the biocompatible electroconductive substance; and c) a movable device contacting the one or more charge generating compositions, wherein movement of the movable device moves the one or more charge generating compositions from a resting state, thereby generating the generated electric charge.

It is the novel and unique interaction of these simple elements which creates the apparatus and methods, within the ambit of the present invention. Pursuant to Title 35 of the United States Code and the Articles of the Patent Cooperation Treaty, descriptions of preferred embodiments follow. However, it is to be understood that the best mode descriptions do not limit the scope of the present invention.

DESCRIPTION OF THE PREFERRED EMBODIMENTS

Figure 1:
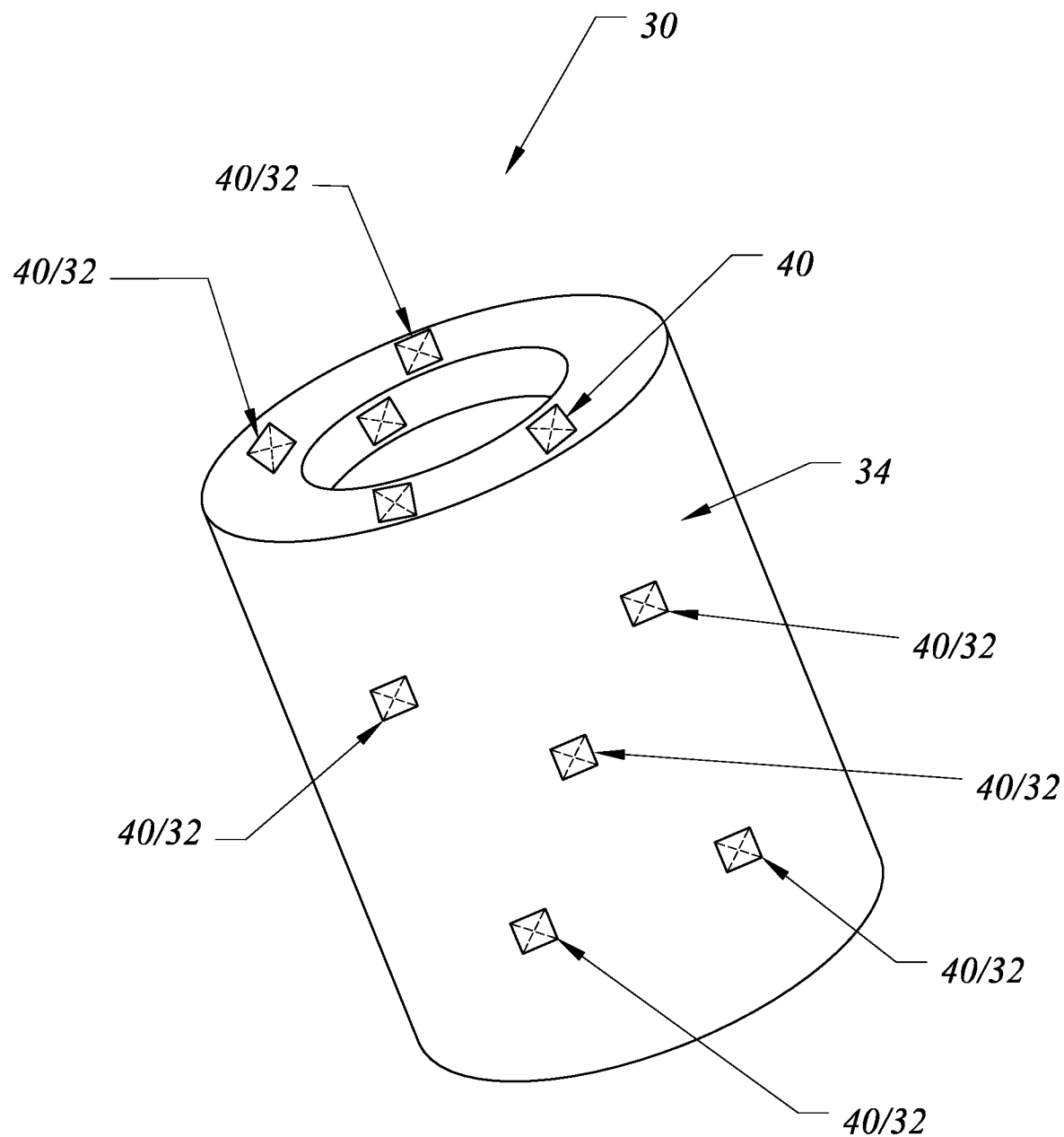
FIG. 1 is a perspective of a preferred embodiment of the implant including a nanogenerator.
Figure 2:
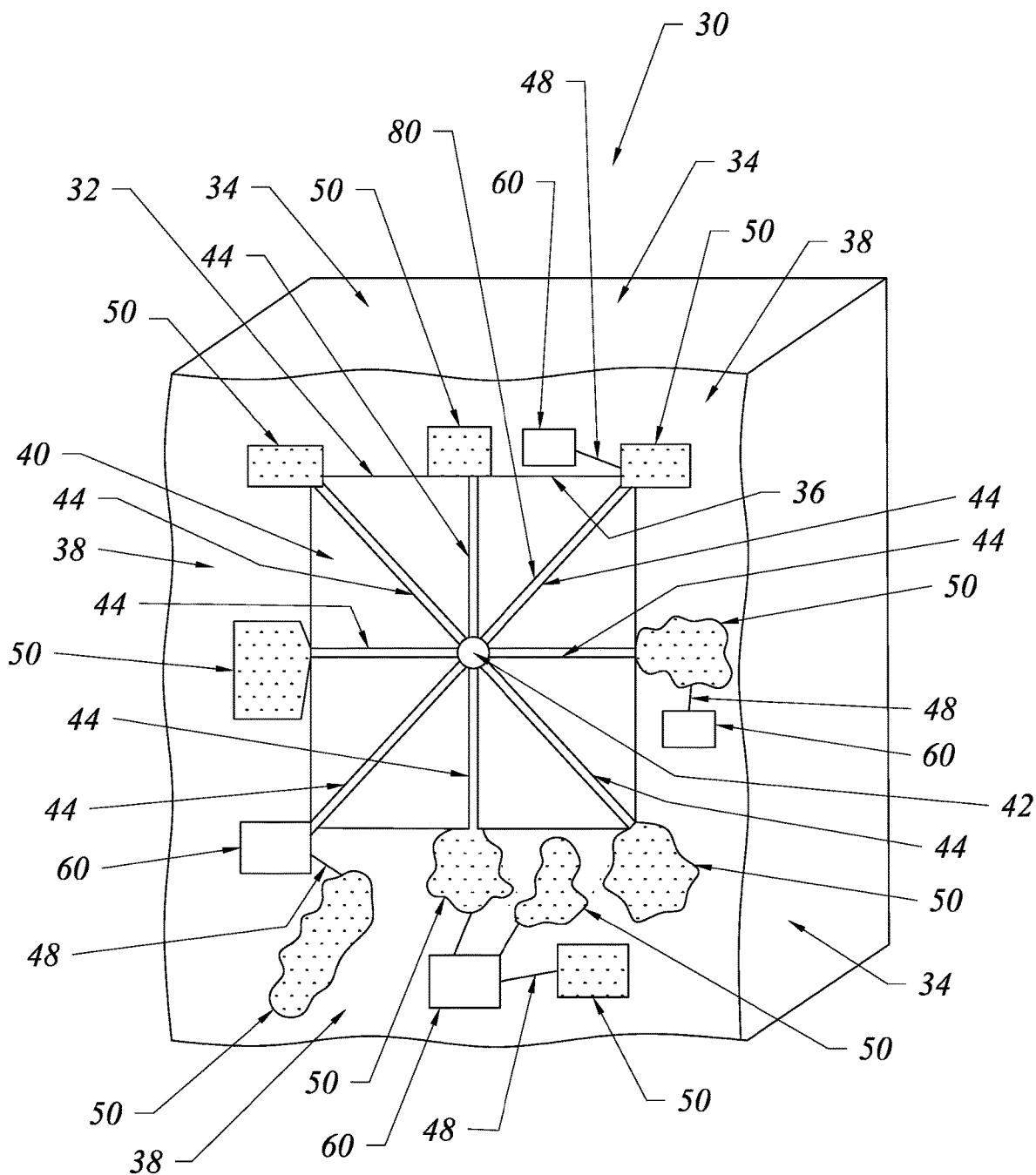
FIG. 2 is a perspective of a preferred embodiment of the nanogenerator of the current implant.

Although the disclosure hereof is detailed to enable those skilled in the art to practice the invention, the embodiments published herein merely exemplify the present invention.

In the most general sense, the present invention is an implant (30) for implantation into a surgically created cavity, a joint space, a tissue or a wound of an animal such as a mammal. Implant (30) includes a nanogenerator (40) including weight (42) that can generate an electric charge as a result of the mammal's movement. Compression, decompression or torsion forces can induce nanogenerator (40) to generate the electrical charge. Implant (30) can be manufactured from any biocompatible metal, polymer, a combination thereof or any other governmentally approved composition for implantation into the human body.

According to the National Institutes of Health's National Library of Medicine, among other things, in the June 2021 edition of the *Journal of Functional Biometerials*, the Abstract declared: "Electrical stimulation (ES) can serve as a therapeutic modality accelerating the healing of wounds, particularly chronic wounds which have impaired healing due to complications from underlying pathology. This review explores how ES affects the cellular mechanisms of wound healing, and its effectiveness in treating acute and chronic wounds. Literature searches with no publication date restrictions were conducted using the Cochrane Library, Medline, Web of Science, Google Scholar and PubMed databases, and 30 full-text articles met the inclusion criteria. In vitro and in vivo experiments investigating the effect of ES on the general mechanisms of healing demonstrated increased epithelialization, fibroblast migration, and vascularity around wounds. Six in vitro studies demonstrated bactericidal effects upon exposure to alternating and pulsed current. Twelve randomized controlled trials (RCTs) investigated the effect of pulsed current on chronic wound healing. All reviewed RCTs demonstrated a larger reduction in wound size and increased healing rate when compared to control groups. In conclusion, ES therapy can contribute to improved chronic wound healing and potentially reduce the financial burden associated with wound management. However, the variations in the wound characteristics, patient demographics, and ES parameters used across studies present opportunities for systematic RCT studies in the future."

The current implant (30) can be provided with an internal nanogenerator capable of generating and distributing a charge to a medical/surgical environment or tissue proximate implant (30). Physical motion or movement causes nanogenerator (40) to generate the electric charge.

Within the scope of the current invention, the nanogenerator's charge generating composition can include one or more metals, carbon molecules or a combination thereof. According to the United States Food and Drug Administration (FDA), current governmentally approved electrically conductive metals for implantation in to humans include gold, nickel-titanium alloy, platinum, silver, stainless steel and titanium, with titanium being the poorest electrical conductor of this group.

Although the FDA has approved select carbon molecules for use in humans, it appears there are limited FDA approved uses of a fullerene, a graphene or a buckypaper. Limited governmental approval at this time does not mean that that the fullerenes, graphenes or buckypapers are not safe to contact human tissue: instead, insufficient testing data is yet to be presented to the FDA. In preferred embodiments of the current implant (30), the fullerenes, graphenes or buckypapers do not contact human tissue.

Carbon allotropes containing sixty perfectly symmetrically arranged carbon atoms include graphenes, fullerenes and buckypapers. Shapes of the carbon nanotubes allotrope determine the degree of the carbon nanotubes electrical conductivity with the angle of the carbon atom lattice controlling whether the carbon nanotube is more or less electrically conductive. Carbon nanotubes have piezoelectric properties where movement generates an electric charge. Movement of the carbon nanotubes can be generated by bending, compression, decompression and torsion forces. In accordance with the current invention, it is believed that the piezoelectric coefficient for a carbon nanotube is about 0.048 C/m2.

With reference to FIGS. 1-4, it is anticipated that the current implant (30) can be implanted into a surgically created cavity, joint space, tissue or wound. Implant (30) is provided with outward surface (34). As shown, nanogenerator (40) capable of generating an electrical charge is positioned within an enclosed chamber or hollow (32) of implant (30). In other preferred embodiments and uses, biocompatible nanogenerator (40) can be a stand-alone device.

Nanogenerator (40) includes weight (42) suspended by a plurality of suspenders (44) connected to an inward wall (36) that surrounds the enclosed chamber or hollow (32). By any means acceptable in the art, suspenders (44) are connected to weight (42) and inward wall (36) of chamber (32) or inner wall (31) of housing (33) of the stand-alone nanogenerator (40).

Suspenders (44) include a charge generating composition (80). Movement of weight (42) causes the charge generating composition to generate electric charge that is deliverable to an outward section (38) of implant (30). Among other things, bending, compression, decompression or torsion forces can cause movement of weight (42).

Outward section (38) of implant (30) is provided with biocompatible electroconductive substance (50) that can transfer an electric charge to a medical/surgical environment, the surgically created cavity, the joint space, the tissue or the wound. In a similar vein, outward surface (34) of housing (33) of stand-alone nanogenerator (40) can be provided with biocompatible electroconductive surface (50).

Select preferred embodiments of implant (30) can optionally include store (60) that is adapted to contain a portion of the electric charge and subsequently supply the stored electric charge to electroconductive substance (50). Conductor (48) can transfer electric charge between the biocompatible electroconductive substance (50) and/or the store (60) and from the store (60) to the biocompatible electroconductive substance (50). Within the scope of the current invention, conductor (48) can be a circuit or other means capable of carrying electric charge about implant (30).

In accordance with the present invention, suspenders (44) and charge generating compositions (80) can include one or more metals, carbon molecules or a combination thereof. Acceptable governmentally approved metals for charge generating compositions (80) are gold, nickel-titanium alloy, platinum, silver, stainless steel and titanium.

Carbon molecules for use in suspenders (44) and charge generating compositions (80) include fullerenes, graphenes, buckypapers or a combination thereof. Depending on medical engineering parameters, select preferred embodiments of charge generating compositions (80) can include multiwalled carbon nanotubes capable of generating an electric charge. Other preferred embodiments of charge generating compositions (80) can include multiwall carbon nanotubes in combination with one or more of the following: single walled carbon nanotubes, buckypaper, graphene and approved metals.

Implant's (30) biocompatible electroconductive substances (50) transferring electric charge can include governmentally approved one or more metals, carbon molecules or a combination thereof. Examples of governmental agencies approving implants for implantation into humans include the US Food and Drug Administration, the Brazilian National Health Surveillance Agency, Health Canada, the China National Medical Products Administration, the European Commission, the Indian Central Drug Standards Control Organisation, the Japanese Pharmaceuticals and Medical Devices Agency, the Philippines Food and Drug Administration and the Russian List of Essential Implantable Medical Devices to name a few of the many. Acceptable metals for biocompatible electroconductive substances (50) are gold, nickel-titanium alloy, platinum, silver, stainless steel and titanium.

Carbon nanotubes are cylindrical molecules manufactured from rolled-up sheets of graphene—a single layer of carbon atoms. Single walled carbon nanotubes typically have diameters of less than one nanometer. Multiwalled carbon nanotubes are interlinked nanotubes and can have diameters of up to about 100 nanometers and lengths ranging from micrometers to millimeters. The bendability/compressibility/decompressability of suspenders (44) can be affected by the arrangement, quantity and type of carbon nanotube utilized to manufacture charge generating compositions (80) utilized in suspenders (44).

The rolling-up direction of the carbon nanotubes determines the electrical conductivity of carbon nanotubes. It is believed that electrical conductivity is associated with the chiral vectors of the carbon nanotubes. For example, armchair like carbon nanotubes have better electrical conductivity than zigzag like carbon nanotubes. It is believed that multi-walled carbon nanotubes conduct charge as well as metals, and possibly better than metals.

Within the scope of the current invention, biocompatible electroconductive substances (50) transferring electric charge can include governmentally approved one or more metals, carbon molecules or a combination thereof.

Figure 3:
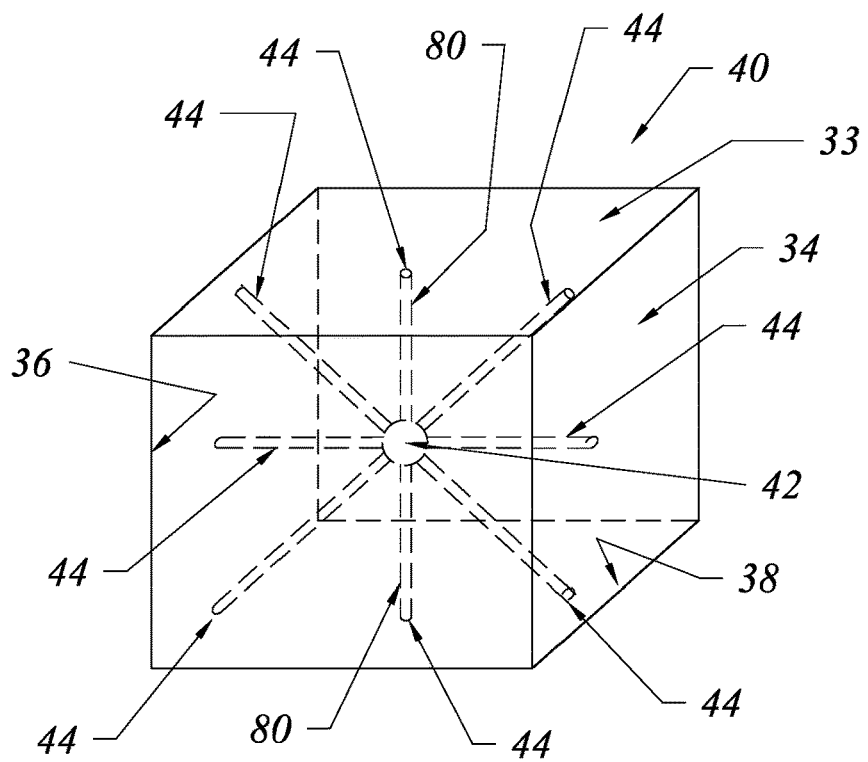
FIG. 3 is a perspective of a preferred embodiment of the biocompatible nanogenerator where the suspenders and weight are shown in phantom.

FIG. 3 is three dimensional perspective of a preferred embodiment of the biocompatible nanogenerator (40) where the suspenders (44) and weight (42) are shown in phantom.

Figure 4:
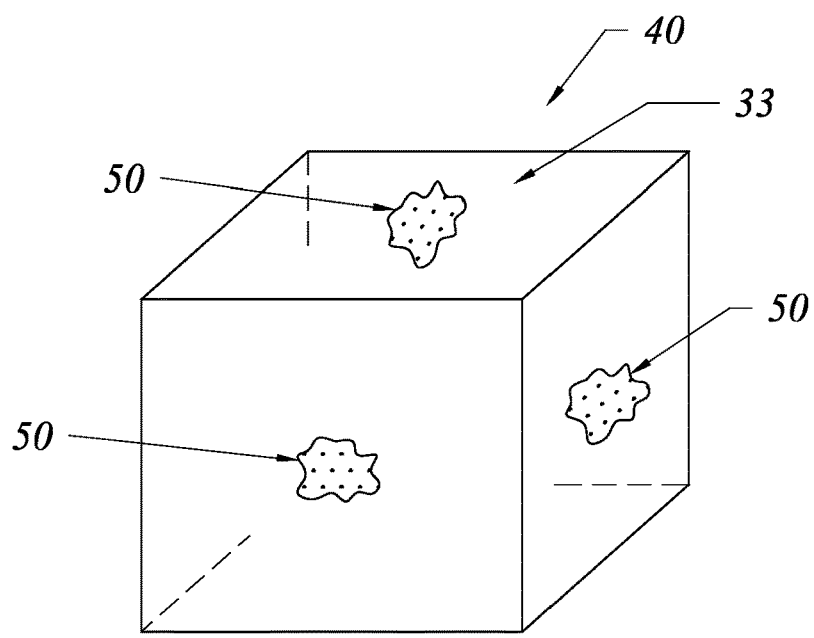
FIG. 4 is a perspective of the biocompatible nanogenerator of FIG. 3 showing the biocompatible electroconductive surface of a stand-alone nanogenerator.

FIG. 4 is a perspective of the biocompatible nanogenerator (40) of FIG. 3 showing the biocompatible electroconductive surface (50) of a stand-alone nanogenerator (40).

Figure 5:
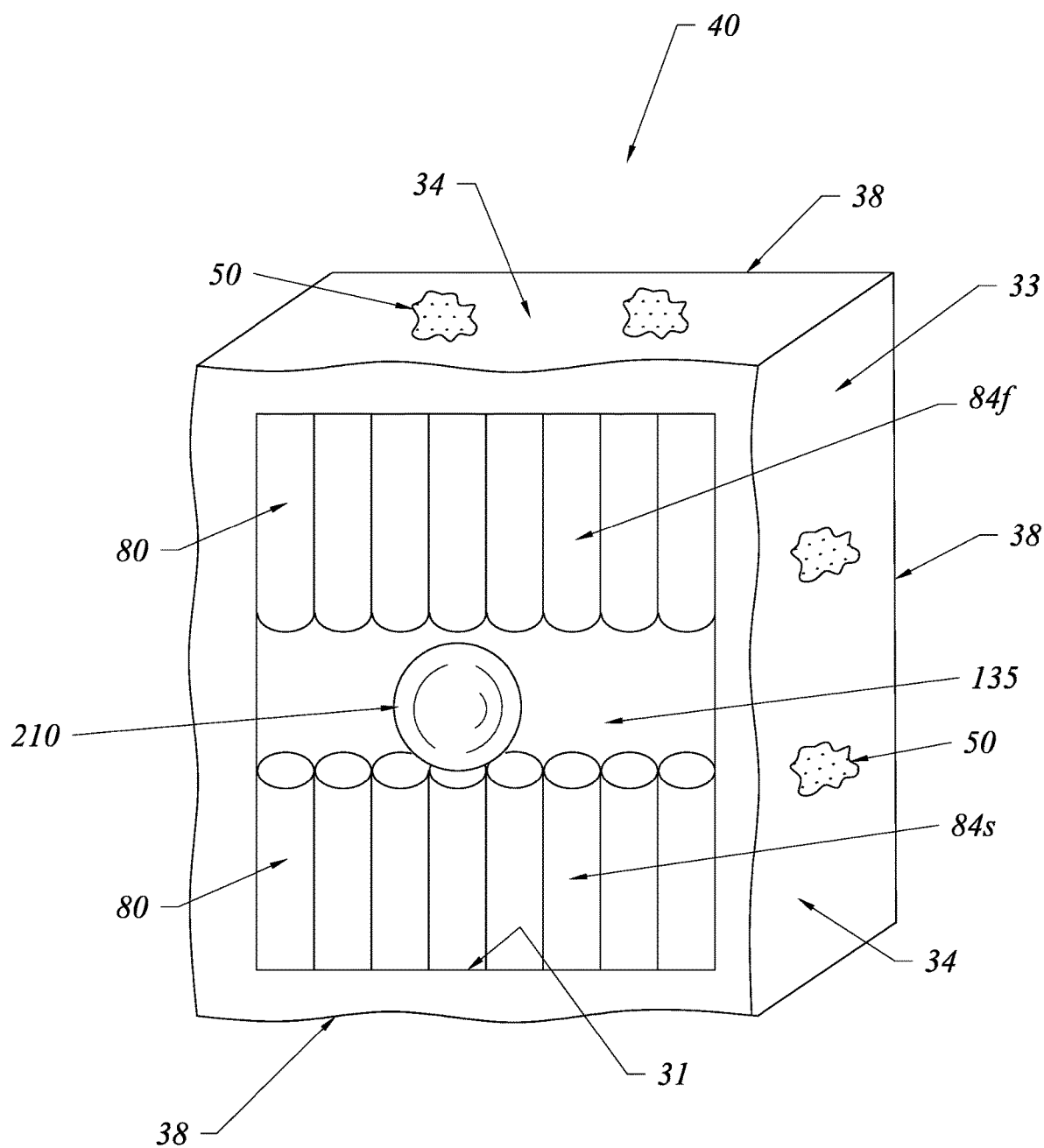
FIG. 5 is a perspective of another preferred embodiment of the nanogenerator using a moveable device to generate an electric charge.

Another preferred embodiment of the current invention is disclosed in FIG. 5. Nanogenerator (40) is provided with housing (33). Housing (33) can be provided with one or more charge generating compositions (80) connected to inner wall (31) of housing (33). Select preferred embodiments can include first rack (84f) and second rack (84s) containing charge generating compositions (80). Charge generating compositions (80) are connected to biocompatible electroconductive substance (50) positioned on outward surface (34) of housing (33). Depending on medical parameters, charge generating compositions (80) can be connected directly to biocompatible electric substance (50) or with an electrical conductor (not shown in FIG. 5).

Space (135) between first rack (84f) and second rack (84s) is provided with ball or cylinder (210) of sufficient weight to compress/move a portion of charge generating composition (80) when moveable device (210) rolls or passes over a portion of charge generating composition (80). Movement of ball or cylinder (210) causes charge generating composition (80) to generate electric charge that can be delivered to biocompatible electroconductive substance (50). Within the scope of the current invention, motion of moveable device (210) alters the charge generating composition (80) relative to the resting state of the charge generating composition (80) and generates the electric charge deliverable to the biocompatible electroconductive substance (50). Select preferred embodiments of stand-alone nanogenerator (40) can be provided with one or more racks (84) and corresponding moveable devices (210).

Stand-alone embodiments of nanogenerator (40) are capable of use in medical/surgical procedures that can involve a surgically created cavity, a joint space, a wound, a tissue or biocompatible additives. In select preferred embodiments, nanogenerator (40) can be delivered to the surgically created cavity, the joint space, the wound, the tissue or the biocompatible additives via a delivery vehicle. Examples of delivery vehicles include but are not limited to bandages, cannulas, creams, dressings, pastes, suspensions, surgical instruments, syringes, etc. Nanogenerators (40) can be delivered to a surgically created cavity, a joint space, a wound, a tissue or biocompatible additives via a delivery vehicle or mixed with the biocompatible additives prior to the delivery of the biocompatible additives to the surgically created cavity, the joint space, the wound or the tissue.

Applicant has enabled, described and disclosed the invention as required by Title 35 of the United States Code and the Articles of the Patent Cooperation Treaty.

What is claimed is:

1. An implant for implantation into a surgically created cavity, a joint space or a wound; the implant comprising:
   a) an outward surface;
   b) a nanogenerator generating an electrical charge; the nanogenerator, positioned within an enclosed chamber of the implant, comprising: a weight suspended by a plurality of suspenders comprising a combination of perpendicular and oblique connections connected to an inward wall surrounding the enclosed chamber; the suspenders comprising a charge generating composition, wherein movement of the weight causes the charge generating composition to generate the electric charge deliverable to an outward section of the device; and
   c) the outward section comprising:
      i) a biocompatible electroconductive substance for transferring the electric charge to the surgically created cavity, the joint space or the wound; and
      ii) optionally, a store adapted to contain a portion of the electric charge and subsequently supply the stored electric charge to the biocompatible electroconductive substance.

2. The implant of claim 1, wherein compression, decompression, distraction or torsion forces or a combination thereof move the weight.

3. The implant of claim 2 comprising a conductor for transferring the electric charge between the biocompatible electroconductive substance and/or the store and from the store to the biocompatible electroconductive substance.

4. The implant of claim 3, wherein the charge generating composition comprises one or more metals, carbon molecules or a combination thereof.

5. The implant of claim 4, wherein:
   a) the metals comprise gold, nickel-titanium alloy, platinum, silver, stainless steel and titanium; and
   b) the carbon molecules comprise a fullerene, a graphene, a buckypaper or a combination thereof.

6. The implant of claim 5, wherein:
   a) the biocompatible electroconductive substance comprises a one or more metals, carbon molecules or a combination thereof; and
   b) the charge generating composition comprises carbon nanotubes.

7. The nanogenerator of claim 6, wherein the compressibility or de-compressibility of one or more of the plurality of suspenders is affected by the quantity of carbon nanotubes.

8. A biocompatible nanogenerator adapted for surgical/medical use; the biocompatible nanogenerator comprising a weight suspended by a plurality of suspenders connected to planar walls of the nanogenerator with at least one perpendicular and one oblique suspender to the remainder of the plurality of suspenders; the suspenders comprising a charge generating composition, wherein movement of the weight causes the charge generating composition to generate and deliver an electric charge to a biocompatible electroconductive substance, positioned on an outward section of housing, for distribution of the electric charge to an environment associated with the surgical/medical use.

9. The biocompatible nanogenerator of claim 8, wherein the charge generating composition comprises one or more metals, carbon molecules or a combination thereof.

10. The biocompatible nanogenerator of claim 9, wherein:
    a) the metals comprise one or more of the group of gold, nickel-titanium alloy, platinum, silver, stainless steel and titanium; and
    b) the carbon molecules comprise one or more of the group of a fullerene, a graphene, a buckypaper or a combination thereof.

11. The biocompatible nanogenerator of claim 10, wherein the carbon molecules comprise carbon nanotubes.

12. The biocompatible nanogenerator of claim 11, wherein the biocompatible electroconductive substance comprises one or more metals, carbon molecules or a combination thereof.

13. The biocompatible nanogenerator of claim 12:
    a) delivered to a surgically created cavity, a joint space, a wound, a tissue or biocompatible additives via a delivery vehicle; or
    b) mixed with the biocompatible additives prior to the delivery of the biocompatible additives to the surgically created cavity, the joint space, the wound or the tissue.

14. A biocompatible nanogenerator adapted for surgical/medical use; the nanogenerator comprising:
    a) a biocompatible electroconductive substance, positioned on an outward section of housing, for distributing a generated electric charge to an environment associated with the surgical/medical use;
    b) a plurality of suspenders comprising one or more charge generating compositions; the plurality of suspenders comprising a combination of perpendicular and oblique connections with an inner wall of enclosed chamber of housing and adapted to generate and deliver the generated electric charge to the biocompatible electroconductive substance; and c) a weight connected with the plurality of suspenders such that movement of the weight moves the plurality of suspenders, thereby generating the generated electric charge.

15. The biocompatible nanogenerator of claim 14, wherein the charge generating composition comprises one or more metals, carbon molecules or a combination thereof.

16. The biocompatible nanogenerator of claim 15, wherein:
   a) the metals comprise one or more of the group of gold, nickel-titanium alloy, platinum, silver, stainless steel and titanium; and
   b) the carbon molecules comprise one or more of the group of a fullerene, a graphene, a buckypaper or a combination thereof.

17. The biocompatible nanogenerator of claim 16, wherein the carbon molecules comprise carbon nanotubes.

18. The biocompatible nanogenerator of claim 17, wherein the biocompatible electroconductive substance comprises one or more metals, carbon molecules or a combination thereof.

19. The biocompatible nanogenerator of claim 18, wherein the biocompatible generator is adapted to be:
   a) delivered to a surgically created cavity, a joint space, a wound, a tissue or biocompatible additives via a delivery vehicle; or
   b) mixed with the biocompatible additives prior to the delivery of the biocompatible additives to the surgically created cavity, the joint space, the wound or the tissue.

* * * * *